United States Patent [19]

Steudle et al.

[11] Patent Number: 4,980,374

[45] Date of Patent: Dec. 25, 1990

[54] DIALYSIS AND RINSING SOLUTION FOR INTRAPERITONEAL ADMINISTRATION WITH ANTIMICROBIAL ACTIVITY

[75] Inventors: Volker Steudle; Volker Bartz, both of Giessen, Fed. Rep. of Germany

[73] Assignee: Fresenius AG, Bad Homburg, Fed. Rep. of Germany

[21] Appl. No.: 337,922

[22] Filed: Apr. 14, 1989

[30] Foreign Application Priority Data

Apr. 15, 1988 [DE] Fed. Rep. of Germany ....... 3812524

[51] Int. Cl.$^5$ ............................................. A61K 31/19
[52] U.S. Cl. .................................................... 514/557
[58] Field of Search ......................................... 514/557

[56] References Cited

U.S. PATENT DOCUMENTS 4,628,050 12/1986 Maeda et al. ...................... 514/167

Primary Examiner—Douglas W. Robinson
Assistant Examiner—Zohreh A. Fay
Attorney, Agent, or Firm—Jack Schuman

[57] ABSTRACT

Peritoneal dialysis solution comprising electrolytes in physiological amounts and at least one osmotically active substance which additionally comprises as antimicrobial substance sorbic acid in an amount of 0.001 to 1% by weight and a pH value of 4 to 7.

8 Claims, 4 Drawing Sheets

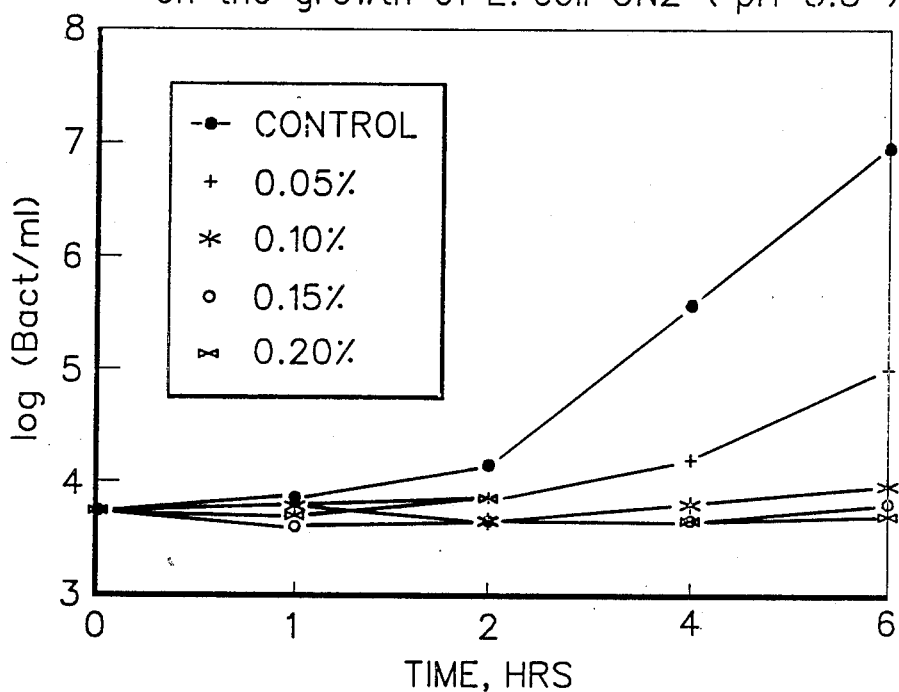
Fig. 1 Effect of sorbic acid in M199 medium on the growth of E. coli-ON2 (pH 5.3)
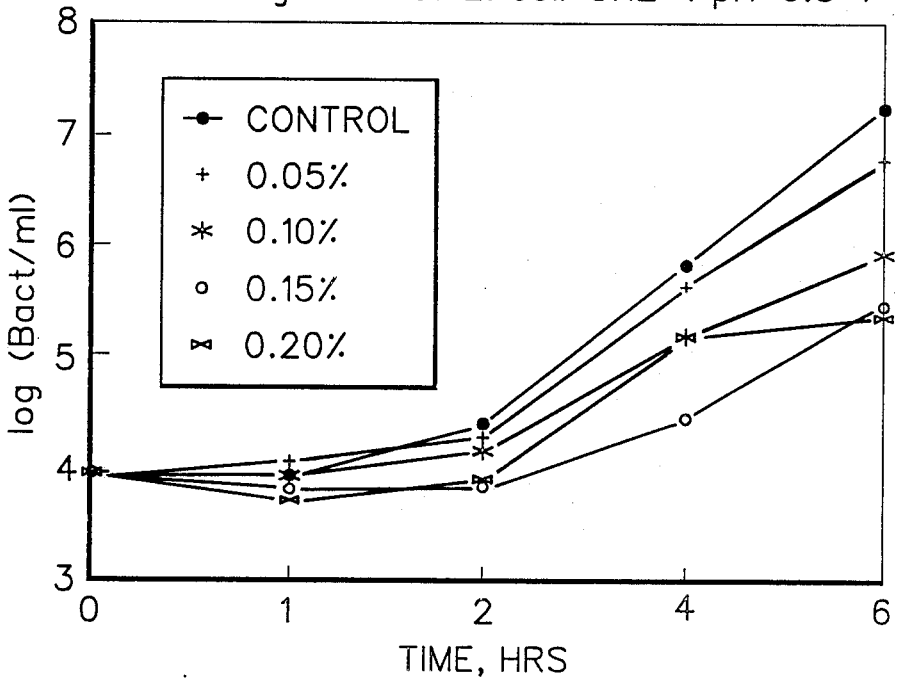
Fig. 2 Effect of sorbic acid in M199 medium on the growth of E. coli-ON2 (pH 6.3)

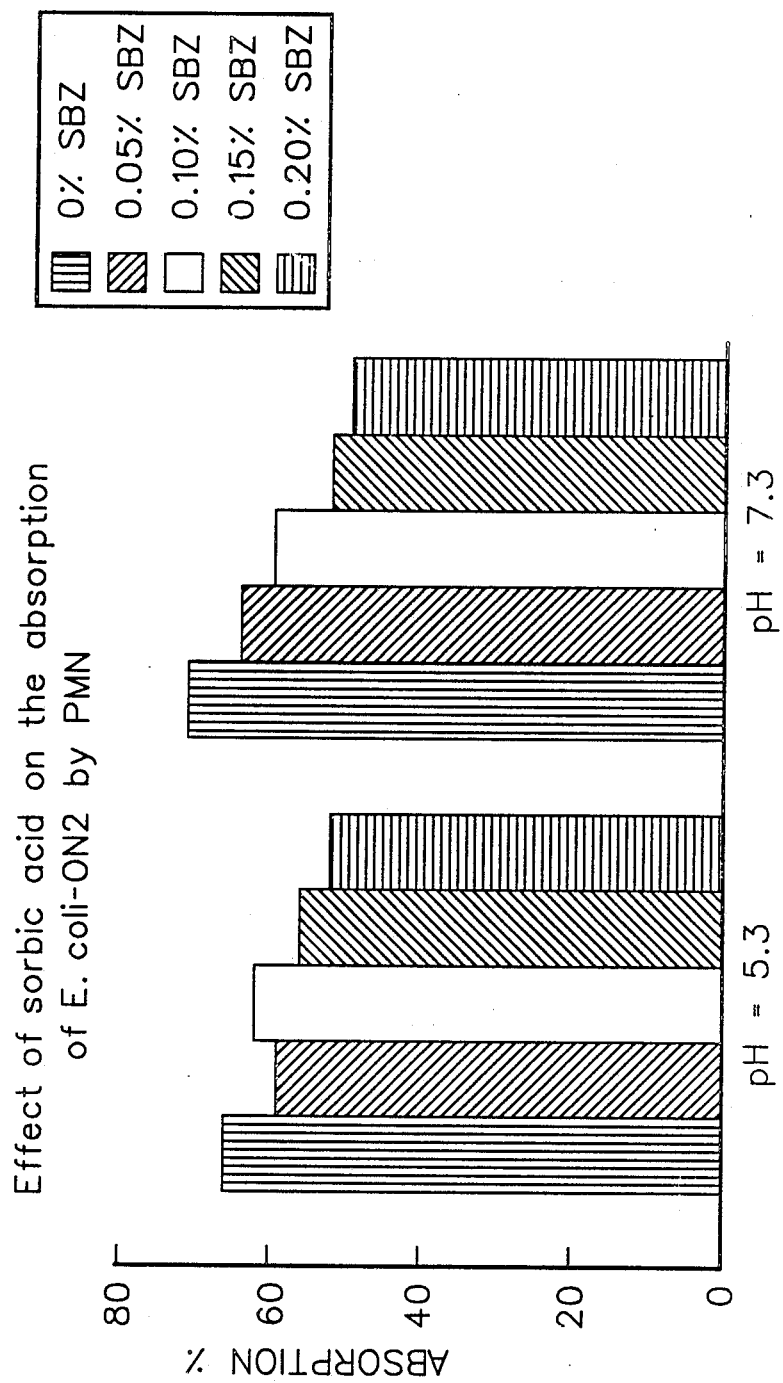

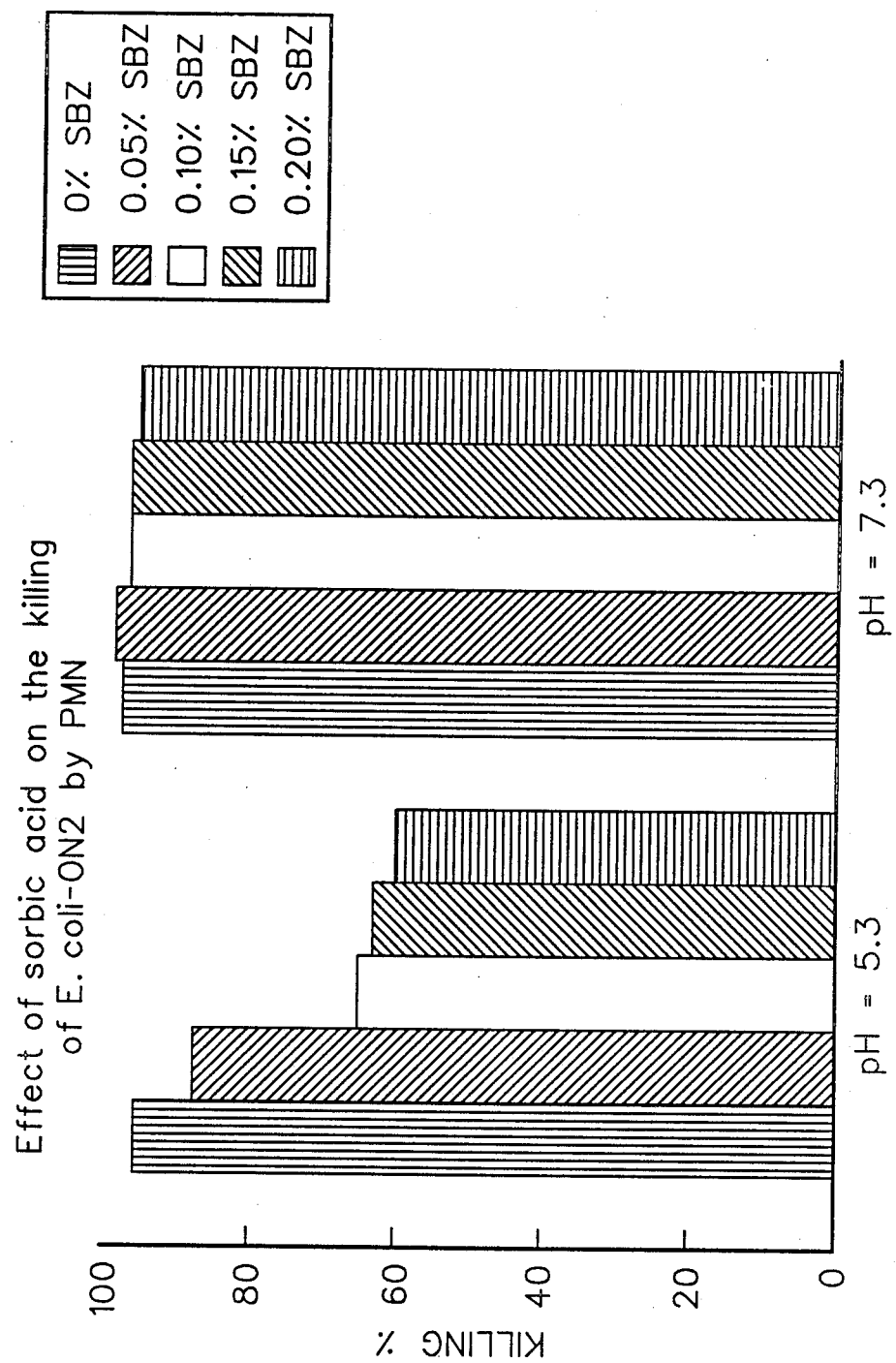

DIALYSIS AND RINSING SOLUTION FOR INTRAPERITONEAL ADMINISTRATION WITH ANTIMICROBIAL ACTIVITY

The subject of the present invention is a dialysis and rinsing or washing solution for intraperitoneal administration containing electrolytes in physiological amounts and at least one osmotically active substance and the use of sorbic acid as antimicrobially active substance in dialysis and rinsing solutions for intraperitoneal administration as well as the use of sorbic acid as antimicrobial substance for preparing a dialysis and rinsing solution for intraperitoneal administration.

In so-called CAPD (continuous ambulant peritoneal dialysis) the peritoneum of patients suffering from kidney disease is filled several times daily with a fresh peritoneal dialysis solution, spent peritoneal dialysis solution being drained to the outside through a catheter. For this purpose, by means of an especially protected connector, which is disposed at the end of an intraperitoneal catheter, a bag with fresh dialysis solution is connected each time, after disconnecting from the connector a bag containing spent dialysis solution. This connection operation must be carried out under absolutely sterile conditions because otherwise there is a danger of germs being entrained through the opened connector. In spite of intense training of the patients and in spite of every conceivable precaution for maintaining sterility, inflammation of the peritoneum repeatedly occurs, i.e. peritonitis, and this therefore represents the major complication in peritoneal dialysis. As explained above it occurs mainly intraluminally by extracorporeal contamination or canalicularly by tunnel infection caused by infiltration of germs in the tunnel region of the intraperitoneal catheter. Infectious peritonitis makes up the major proportion of the peritonitis which occurs in peritoneal dialysis and which can be treated only under massive administration of antibiotics and moreover make it necessary to terminate the CAPD and connect the patient to a hemodialysis machine.

To avoid germ infiltration or invasion and to considerably reduce the danger of peritonitis specially constructed connectors have been proposed in which the connection regions cannot be touched (DE-PS 2,853,635). In addition, preformed intraperitoneal catheters have been proposed for eliminating the pressure stress of the catheter in the implantation passage (DE-PS 3,147,722). Also, heating means have been proposed for sterilizing the plugged-together connector (DE-OS 3,601,893). Finally, special connectors have been proposed which before introduction of the solution into the peritoneum permit flushing of the connector and thus washing out of germs (DE-OS 3,513,204 and 3,513,205)

Nevertheless, the risk of peritonitis in CAPD has still not been completely eliminated.

Such peritonitis is most frequently induced by *Staphylococcus epidermidis* with mild course and by *Staphylococcus aureus* with serious and tedious course. The infection paths with these pathogens are usually transluminal through the opened connector and catheter because 3 to 4 times a day when the dialysate is changed penetration of germs via air, dust, droplets and by direct contact with the connector inner side is possible through the opening of the system.

Apart from the invasion of germs along the catheter due to a tunnel effect, infections are observed via perforated and inflamed organs in the abdominal cavity and ascending infections from the genital tract in women through the fallopian tubes. Furthermore, hematogenic dissemination is observed Finally, mycotic infections with *Candida albicans* as most frequent pathogen play a part in post-operative diffuse peritonitis.

Ideal growth (reproduction) conditions exist for intraperitoneally infiltrating microorganisms, especially since the irrigation or rinsing solutions employed comprise almost exclusively glucose as osmotically active substance and glucose guarantees excellent growth conditions for microbes. The objective of a peritonitis prophylaxis is therefore to prevent penetration of microorganisms into the peritoneal cavity or to inhibit their growth intraperitoneally.

The invention is therefore based on the problem of providing a dialysis and rinsing solution of the type mentioned at the beginning which can be administered to patients intraperitoneally over a long period of time and minimizes as far as possible, or even prevents, and danger of an infectious peritonitis complication This problem is solved by a dialysis and rinsing solution which is characterized by an antimicrobial content of sorbic acid and a pH value of 4 to 7.

It has now surprisingly been found that the use of sorbic acid in peritoneal dialysis solutions inhibits the growth of germs which have invaded the peritoneal cavity to such an extent that endogenous immune forces can successfully come into action, i e. peritonitis can be effectively prevented.

Sorbic acid, which has the formula

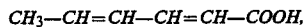

$$CH_3-CH=CH-CH=CH-COOH,$$

is the 4,2-hexadiene acid or 2-propylene acrylic acid with the empirical formula

$$C_6H_8O_2.$$

Sorbic acid has an antimicrobial effect which is usually based on the undissociated lipoid-soluble form. In this respect the use of sorbic acid thus depends on the pH value.

Sorbic acid is of course used for the conservation of foodstuffs and other utility articles. According to pages 841 to 843 of the Lexikon der Hilfsstoffe fuer Pharmazie, Kosmetik und angrenzende Gebiete, H. Fiedler, 1981, Vol. 9 (OVR Oberschwaebische Verlagsanstalt Ravensburg), sorbic acid is recommended as preservative for pharmaceutical and cosmetic preparations and the use thereof for preserving foodstuffs is described. In DE-AS 1,198,659 specific mixed anhydrides comprising sorbityl radicals are proposed, such as sorbic acid-ethylcarbonic acid anhydride, sorbic acid-acetic acid anhydride and propionic acid-scorbic acid anhydride as preservatives for conserving perishable substances of vegetable or animal origin, such as foodstuffs, injection solutions and other pharmaceutical or cosmetic preparations, and the microbicidal effect of these anhydrides is said to be superior to sorbic acid.

According to the invention the use of sorbic acid is preferred in the weakly acid range (pH 5 to 6) but the use is not restricted solely to this preferred range. Thus, pH values of 4 to 7 can also be considered practicable; a pH value of 4 can under certain circumstances already lead to irritations of the mucous membrane of the peritoneum and due to the very weak dissociation (only about 0.7% of the sorbic acid is present undissociated)

the pH value of 7 necessitates a higher starting concentration of sorbic acid.

According to the invention in the peritoneal dialysis solution 0.001 to 1% by weight sorbic acid is employed, sorbic acid according to the invention referring to the undissociated component. Said component can be easily calculated on the basis of the pH value employed and the pK constant of sorbic acid of $1.73 \times 10^{-5}$.

Consequently, apart from pure sorbic acid the salts thereof with bases, for example sodium, potassium or calcium sorbate, can be used which after dissolving in water and setting of the pH value with the aid of acids (hydrochloric acid) break down into the corresponding non-dissociated component of the sorbic acid and the remaining dissociated components.

As already observed above sorbic acid is widely used for preserving foodstuffs. Sorbic acid is a fatty acid and is therefore completely metabolized in the human organism, just like any other fatty acid. In this respect excellent biocompatibility is ensured when using sorbic acid in peritoneal dialysis solutions. Consequently, there is no problem of the accumulation of sorbic acid in the human organism due to difficult metabolization, as is the case for example with sugar substitute substances (sorbite, xylite) or polymeric sugars.

Depending on the concentration employed, sorbic acid has a good fungistatic or fungicidal effect and can for example inhibit relatively well the growth of microorganisms, such as Candida albicans, or kill them. Furthermore, the bacteriostatic or bactericidal effect is also good, at least at a pH value of 6. Thus, microorganisms such as Staphylococcus aureus, Klebsiella pneumoniae, E. coli and the like are inhibited in growth by even small inhibition concentrations (cf. FIGS. 1 and 2).

Generally, it suffices for the sorbic acid to be present in a concentration which inhibits growth because the body can for example easily manage a germ amount of 100 with its own defence mechanisms, for example by macrophages. By using sorbic acid the inherent defence mechanism, for example by macrophages or polymorphonuclear leucocytes, is practically not reduced (at higher pH value) or reduced only to a slight extent (at lower pH value, for example pH 5.3). This means that when using sorbic acid according to the invention the body's own defence mechanisms continue to be effective (cf. FIGS. 3 and 4).

The aforementioned pH value of the dialysis solution according to the invention can be set with the aid of lactic acid or acetic acid in conjunction with sodium hydroxide solution, lactic acid being preferred. Preferably, the dialysis solution has a pH value of 5.6 at a lactate concentration of 35 mmol/l.

However, other usual organic or inorganic acids can be employed to set the pH value, provided they are accepted by the human body.

Sorbic acid is an easily obtainable cheap commercial product. It usually has a purity degree of more than 99%. Furthermore, it can be heat-sterilized without any problems, i.e. heated to the usual sterilization temperature of 115 to 122° C.

The dialysis and rinsing or irrigation solution according to the invention consists of a mixture of solutions which are available commercially or otherwise mentioned in the literature except for the fact that to said solutions as antimicrobial substance sorbic acid or its salts are added in the aforementioned concentration of 0.001 to 1% by weight.

To be physiologically neutral, the solutions available on the market contain electrolyte salts with physiological level.

The ion concentrations in the dialysis and rinsing solution according to the invention are advantageously 125 to 150, more especially 132 to 140 mmol/l $Na^+$; 0 to 8, more especially to 4 mmol/l $K^+$; 0 to 3, more especially 0.5 to 2 mmol/l $Ca^{++}$; 0 to 2.5, more especially 0.3 to 1 mmol/l $Mg^{++}$; 10 to 60, more especially 30 to 50 mmol/l ions, selected from the group lactate, acetate and biocarbonate ions and the remainder $Cl^-$.

Furthermore, the dialysis and rinsing solution according to the invention contains an osmotically active substance in osmotically active amounts. By far the most widely used osmotically active substance is glucose, the idea underlying the invention not covering the use of such a substance. In this respect all other substances discussed at present can be used as osmotically active substance. Reference is made to the patent application filed by the same Applicants on the same date with the title "Dialysis and rinsing solution for intraperitoneal administration" (P 38 12 525.0-35, which suggests the use of galactose as osmotically active substance and otherwise explains further osmotically active substances.

These substances occur in osmotically active amounts so that the osmotic pressure lies between 300 to 700, more especially 320 to 550, and preferably 350 to 450 mosm/l.

Thus, a peritoneal dialysis solution comprising 16.5 g or 46.76 g/l alactose hydrate has a theoretical osmotic pressure of 355 and 507 mosm/l respectively which is by the way somewhat increased by the small amount of sorbic acid compared therewith.

Likewise, usual additives, for example insulin and the like, can be employed in the dialysis solution according to the invention. Their use is also not covered by the idea according to the invention.

The following example explains the invention.

EXAMPLE

In 1 l water of injection quality a solution of glucose as osmotically active substance, electrolyte salts in the form of the lactate, acetate or chloride and sorbic acid or its salts is prepared and thereafter a bag is filled therewith and heat-sterilized.

The solution has the following composition:

| | |
|---|---|
| $Na^+$ | 132.00 mmol/l |
| $Ca^{2+}$ | 1.75 mmol/l |
| $Mg^{2+}$ | 0.75 mmol/l |
| $Cl^-$ | 102.00 mmol/l |
| Lactate | 35.0 mmol/l |
| Glucose | 16.5 g/l |
| Sorbic acid | 1.0 g/l |

The theoretical osmotic pressure is 355 mosm/l whilst the sorbic acid concentration is 0.1% by weight.

Investigation of the effectiveness of sorbic acid or bacteria and the effects of sorbic acid on phagocytosis and the intracellular killing of bacteria by polymorphonuclear leucocytes In these investigations sorbic acid solutions were used in culture medium M199. Sorbic acid is easily soluble in this medium M199 on application of heat as generated for example by a microwave oven. In these investigations concentrations of sorbic acid of 0.05% to 0.2%

(weight/volume) were employed. The control medium used was sorbic-acid-free culture medium M199.

The investigation of the effect of sorbic acid on the proliferation of bacteria was carried out with E. coli-ON2, a well-defined strain of E. coli. The results obtained in this investigation are summarized in the following Table 1 and shown graphically in FIGS. 1 and 2. It can be seen both from Table 1 and from FIGS. 1 and 2 that the sorbic acid is bacteriostatically effective against E. coli-ON2, the effectiveness being greater at pH 5.3 than at pH 6.3.

The effect of sorbic acids on the phagocytosis and the intracellular killing by polymorphonuclear leucocytes were investigated using the same E. coli strain with the aid of human polymorphonuclear leucocytes (PMN). The same culture medium as employed for the above investigations was used. The measurements were carried out after 60 minutes incubation of PMN with E. coli-ON 2, both at pH 5.3 and at pH 7.3. The results obtained in these tests are summarized in Table 2 and graphically represented in FIGS. 3 and 4. The results show that by using sorbic acid the bacteriocidal effectiveness of PMN is only slightly impaired. The bacteriocidal effectiveness of PMN is maintained, although to a somewhat reduced extent, even at pH 5.3.

TABLE I

Effect of sorbic acid on the growth of E. coli-ON2 in M199 medium

| | | Mean growth of E. coli-ON2 (log CUF/ml) ± SEM[a] | |
|---|---|---|---|
| | hrs. | pH 5,3 | pH 6,3 |
| 0% SBZ | 0 | 3.73 ± 0.03 | 3.95 ± 0.09 |
| | 1 | 3.84 ± 0.09 | 3.96 ± 0.08 |
| | 2 | 4.12 ± 0.13 | 4.39 ± 0.05 |
| | 4 | 5.60 ± 0.10 | 5.90 ± 0.05 |
| | 6 | 6.94 ± 0.08 | 7.33 ± 0.13 |
| 0,05% SBZ | 0 | 3.73 ± 0.03 | 3.95 ± 0.09 |
| | 1 | 3.78 ± 0.06 | 4.07 ± 0.21 |
| | 2 | 3.78 ± 0.11 | 4.30 ± 0.17 |
| | 4 | 4.18 ± 0.16 | 5.68 ± 0.10 |
| | 6 | 5.03 ± 0.39 | 6.88 ± 0.23 |
| 0,10% SBZ | 0 | 3.73 ± 0.03 | 3.95 ± 0.09 |
| | 1 | 3.76 ± 0.05 | 3.94 ± 0.06 |
| | 2 | 3.68 ± 0.06 | 4.18 ± 0.07 |
| | 4 | 3.77 ± 0.06 | 5.25 ± 0.15 |
| | 6 | 3.93 ± 0.09 | 6.03 ± 0.06 |
| 0,15% SBZ | 0 | 3.73 ± 0.03 | 3.95 ± 0.09 |
| | 1 | 3.57 ± 0.10 | 3.84 ± 0.20 |
| | 2 | 3.65 ± 0.10 | 3.87 ± 0.14 |
| | 4 | 3.63 ± 0.06 | 4.51 ± 0.03 |
| | 6 | 3.77 ± 0.15 | 5.57 ± 0.10 |
| 0,20% SBZ | 0 | 3.73 ± 0.03 | 3.95 ± 0.09 |
| | 1 | 3.68 ± 0.03 | 3.71 ± 0.11 |
| | 2 | 3.84 ± 0.05 | 3.94 ± 0.10 |
| | 4 | 3.64 ± 0.05 | 5.25 ± 0.39 |
| | 6 | 3.68 ± 0.03 | 5.48 ± 0.06 |

[a] on the basis of at least 3 separate experiments

TABLE 2

Effect of sorbic acid on phagocytosis and the intracellular killing of E. coli-ON2 by polymorphonuclear leucocytes

| pH | SBZ (%) in M199 | Phagocytosis (%)[a] | Killing (%)[b] |
|---|---|---|---|
| 5,3 | 0 | 66 ± 5 | 96 ± 1 |
| | 0.05 | 59 ± 5 | 88 ± 3 |
| | 0.10 | 62 ± 5 | 65 ± 13 |
| | 0.15 | 56 ± 5 | 63 ± 12 |
| | 0.20 | 52 ± 7 | 60 ± 19 |
| 7,3 | 0 | 71 ± 4 | 98 ± 1 |
| | 0.05 | 64 ± 6 | 99 |
| | 0.10 | 60 ± 6 | 97 ± 1 |
| | 0.15 | 52 ± 4 | 97 ± 1 |
| | 0.20 | 50 ± 7 | 96 ± 1 |

[a] The results are expressed as average values ± SEM and are based on ten separate experiments carried out in duplicate.
[b] The results are expressed as average values ± SEM and are based on three separate experiments carried out in duplicate.

We claim:

1. The method for preventing bacterial infection comprising applying to the intraperitoneal cavity an isotonic dialysis solution comprising at least one osmotically active substance and an antimicrobially effective amount of sorbic acid, said solution having a pH value of 4 to 7.

2. The method as in claim 1, wherein the sorbic acid concentration in said solution is between 0.001 and 1 percent by weight.

3. The method as in claim 1, wherein the sorbic acid concentration in said solution is between 0.05 and 0.2 percent by weight.

4. The method as in claim 1, wherein said solution has a pH value of 5 to 6.

5. The method as in claim 1, wherein said solution has a pH value of 5.6.

6. The method as in claim 1, wherein the pH value of said solution is set by the addition to said solution of material from the group consisting of organic acids and inorganic acids accepted by the body of the patient.

7. Method as in claim 4, wherein the pH value of said solution is set by the addition to said solution of material from the group consisting of lactic acid, acetic acid, sodium hydroxide, and salts thereof.

8. Method as in claim 1, wherein aid solution has a pH value of 5.6 and a lactate concentration of 35 mmol/l.

* * * * *

UNITED STATES PATENT AND TRADEMARK OFFICE
CERTIFICATE OF CORRECTION

PATENT NO. : 4,980,374
DATED : December 25, 1990
INVENTOR(S) : Volker Steudle and Volker Bartz It is certified that error appears in the above-identified patent and that said Letters Patent is hereby corrected as shown below:

```
Column 2, line 4, after "observed" add --.--.
Column 2, line 55, after "propionic acid-" delete
"scorbic acid" and substitute therefor --sorbic acid--.
Column 4, line 31, after "46.76 g/l" delete "alactose"
and substitute therefor --galactose--.
Column 6, line 10, add as a footnote to "Table 1 -
continued" after "a on the basis of at least 3 separate
experiments" the words --SBZ: sorbic acid--.
Claim 7, line 1, after "Method as in claim" delete "4"
and substitute therefor --1--.
Claim 8, line 1, before "solution" delete "Method as in
claim 1, wherein aid" and substitute therefor --Method as
in claim 1, wherein said--.
```

Signed and Sealed this

Fifth Day of May, 1992

Attest:

DOUGLAS B. COMER

*Attesting Officer*    Acting Commissioner of Patents and Trademarks